(12) United States Patent
Azarsa et al.

(10) Patent No.: US 11,298,286 B2
(45) Date of Patent: Apr. 12, 2022

(54) REHABILITATION SYSTEM FOR ROBOTIZED MOBILIZATION OF A GLENOHUMERAL JOINT

(71) Applicants: Mohammad Hassan Azarsa, Tehran (IR); Alireza Mirbagheri, Tehran (IR); Azadeh Shadmehr, Tehran (IR); Noureddin Karimi, Tehran (IR)

(72) Inventors: Mohammad Hassan Azarsa, Tehran (IR); Alireza Mirbagheri, Tehran (IR); Azadeh Shadmehr, Tehran (IR); Noureddin Karimi, Tehran (IR)

(73) Assignee: SINA ROBOTICS & MEDICAL INNOVATORS CO. LTD., Tehran (IR)

( * ) Notice: Subject to any disclaimer, the term of this patent is extended or adjusted under 35 U.S.C. 154(b) by 328 days.

(21) Appl. No.: 16/356,029

(22) Filed: Mar. 18, 2019

(65) Prior Publication Data
US 2019/0209411 A1 Jul. 11, 2019

Related U.S. Application Data

(60) Provisional application No. 62/644,503, filed on Mar. 18, 2018.

(51) Int. Cl.
*A61H 1/02* (2006.01)
*B25J 11/00* (2006.01)
*B25J 13/08* (2006.01)
*A61B 8/08* (2006.01)

(52) U.S. Cl.
CPC ............ *A61H 1/0281* (2013.01); *B25J 11/00* (2013.01); *B25J 13/088* (2013.01); *A61B 8/0875* (2013.01); *A61H 2201/149* (2013.01); *A61H 2201/1638* (2013.01); *A61H 2201/1666* (2013.01); *A61H 2201/501* (2013.01); *A61H 2201/5061* (2013.01); *A61H 2203/0456* (2013.01)

(58) Field of Classification Search
CPC ............ A61H 1/0281; A61H 2201/149; A61H 2201/1638; A61H 2201/1666; A61H 2201/501; A61H 2201/5061; B25J 11/00; B25J 13/088
See application file for complete search history.

(56) References Cited

U.S. PATENT DOCUMENTS

| | | | | |
|---|---|---|---|---|
| 5,179,939 A | * | 1/1993 | Donovan | A61H 1/0281 482/4 |
| 5,911,695 A | * | 6/1999 | Watkins | A61B 5/103 600/587 |
| 2007/0225620 A1 | * | 9/2007 | Carignan | A61H 1/0281 601/5 |

(Continued)

*Primary Examiner* — Timothy A Stanis
(74) *Attorney, Agent, or Firm* — Bajwa IP Law Firm; Haris Zaheer Bajwa

(57) ABSTRACT

A rehabilitation system for robotized mobilization of a human glenohumeral joint of a patient. The rehabilitation system may include a limb gripping member and an actuating mechanism. The limb gripping member may be configured to receive an arm of a patient and secure the arm of the patient in a predetermined position. The actuating mechanism may be configured to urge a head of a humerus bone of the patient to glide along a first axis by applying a linear force to a proximal end of the humerus bone of the patient.

11 Claims, 6 Drawing Sheets

(56) References Cited

U.S. PATENT DOCUMENTS

| | | | | |
|---|---|---|---|---|
| 2009/0149783 | A1* | 6/2009 | Nef | A63B 23/03508 |
| | | | | 601/5 |
| 2012/0330198 | A1* | 12/2012 | Patoglu | B25J 9/0006 |
| | | | | 601/33 |
| 2013/0190662 | A1* | 7/2013 | Stevenot | A63B 21/4045 |
| | | | | 601/33 |
| 2013/0237883 | A1* | 9/2013 | Malosio | A61H 1/0274 |
| | | | | 601/33 |
| 2014/0336542 | A1* | 11/2014 | Fu | A61H 1/0277 |
| | | | | 601/5 |
| 2019/0290526 | A1* | 9/2019 | Horosko | A61H 9/0078 |

* cited by examiner

REHABILITATION SYSTEM FOR ROBOTIZED MOBILIZATION OF A GLENOHUMERAL JOINT

CROSS-REFERENCE TO RELATED APPLICATION

This application claims the benefit of priority from U.S. Provisional Patent Application Ser. No. 62/644,503 filed on Mar. 18, 2018, and entitled "AN APPARATUS FOR ROBOTIC MOBILIZATION OF GLENOHUMERAL JOINT" which is incorporated herein by reference in its entirety.

TECHNICAL FIELD

The present disclosure generally relates to physical therapeutic robots, and particularly to a rehabilitation system for robotized mobilization of a human glenohumeral joint of a patient.

BACKGROUND

Nowadays, in order to improve and optimize techniques of musculoskeletal and neuromotor rehabilitation of limbs of the human body, motorized systems able to assist a patient in different movements necessary to recover the limb to be rehabilitated are used. More precisely, known biomedical devices of a robotized type which are able to interact with a patient, thus ensuring that a movement of a musculoskeletal apparatus follows physiological movement of a treated limb and of a joints involved in the movement are generally used. Also, other devices are intended for accurately measuring of the stiffness and quantify its components (force and displacement), and ultimately improve the evaluation and diagnosis of the joint conditions.

While existing devices have attempted to address these issues, these have not been applicable to relieve "joint hypomobility". Joint hypomobility is one of the most common complications in the musculoskeletal and neurologic disorders, especially in the glenohumeral joint, in which the intra-articular movements (accessory movement or arthrokinematics) decrease. The joint hypomobility generally refers to decreased capsular mobility. Subsequently, the patient's ability in the osteokinematics and the joint range of motion is reduced.

Joint mobilization is a physical therapy procedure for treating patients with the joint hypomobility. This manual therapeutic maneuver causes mobilizing the joint surfaces, restoring the arthrokinematic movements, and increasing joint flexibility and range of motion. Furthermore, the joint mobilization increases arthrokinematic movements and stretching of musculotendinous and capsuloligamentous tissues of the joint in the clinical usages and therapeutic goals.

Nevertheless, an articulation of a shoulder is viewed, in some relatively simple conventional devices, as a merely spherical joint without taking account of actual kinematic movement of a shoulder girdle. In fact, in the shoulder hypomobility, translational motions of the center of instantaneous rotation are not possible. There is, therefore, a need for a rehabilitation system for robotized mobilization of a human glenohumeral joint of a patient that enables translational motions of a center of instantaneous rotation in order to allow combined rotary and translational motion of an actual center of instantaneous rotation of a shoulder.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

According to an exemplary embodiment, the present disclosure describes a rehabilitation system for robotized mobilization of a human glenohumeral joint of a patient. In an exemplary embodiment, the exemplary rehabilitation system may include a limb gripping member, and an actuating mechanism.

In an exemplary embodiment, the limb gripping member may be configured to receive an arm of the patient, and secure the arm of the patient in a predetermined position. In an exemplary embodiment, the actuating mechanism may be configured to urge a head of a humerus bone of the patient to glide along a first axis by applying a linear force to a proximal end of the humerus bone of the patient. In an exemplary embodiment, the head of the humerus bone may be located at the proximal end of the humerus bone of the patient.

In an exemplary embodiment, the limb gripping member may be mounted slidably onto the guide rail. In an exemplary embodiment, the guide rail may be configured to limit movements of the patient's arm and the limb gripping member to a linear movement along a second axis.

In an exemplary embodiment, the limb gripping member may include a crescent-shaped section configured to grasp the arm of the patient. In an exemplary embodiment, the limb gripping member may also include a groove-shaped section configured to secure the arm and an elbow of the patient.

In an exemplary embodiment, the actuating mechanism may further include a force applying assembly, and an actuator. In an exemplary embodiment, the force applying assembly may be mounted slidably onto the guide rail. In an exemplary embodiment, the guide rail may be configured to limit movements of the force applying assembly to a linear movement along the second axis.

In an exemplary embodiment, the actuator may be configured to apply a linear force along the first axis to the proximal end of the humerus bone of the patient through moving the force applying assembly on the guide rail and along the second axis. In an exemplary embodiment, the first axis may be parallel to the second axis.

In an exemplary embodiment, the force applying assembly may include a stylus and a force measuring member. In an exemplary embodiment, the stylus may be configured to contact the arm of the patient and push the head of the humerus bone to glide along the first axis responsive to the actuator moving the force applying assembly on the guide rail and along the second axis. In an exemplary embodiment, the stylus may further be configured to be aligned with the head of the humerus bone of the patient responsive to the arm of the patient inserted into the limb gripping member.

In an exemplary embodiment, the force measuring member may be disposed between the actuator and the stylus. In an exemplary embodiment, the force measuring member may be configured to measure the linear force applied to the proximal end of the humerus bone of the patient from the stylus. Furthermore, in an exemplary embodiment, the force measuring member may further be configured to transmit a first set of data to one or more processors associated with the measured linear force applied to the proximal end of the humerus bone of the patient from the stylus. In an exemplary embodiment, the force measuring member may include one of a dynamometer and a load cell.

In an exemplary embodiment, the actuating mechanism may further include an encoder coupled to the actuator. In an exemplary embodiment, the encoder may be configured to measure an amount of the linear movement of the force applying assembly along the second axis. In an exemplary embodiment, the encoder may be further configured to transmit a second set of data to the one or more processors associated with the linear movement of the force applying assembly along the second axis.

In an exemplary embodiment, the rehabilitation system may further include an ultrasound imaging system. In an exemplary embodiment, the ultrasound imaging system may be configured to Capture a third set of data associated with position of the head of the humerus bone along the first axis. In an exemplary embodiment, the ultrasound imaging system may further be configured to transmit the third set of data to the one or more processors. In an exemplary embodiment, the third set of data may include at least one ultrasound image of the head of the humerus bone of the patient.

In an exemplary embodiment, the one or more processors may be further configured to receive the first set of data, receive a second set of data, receive a fourth set of data, and transmit a fourth set of data to the actuator based on the received first set of data, the received second set of data, and the received third set of data. In an exemplary embodiment, the one or more processors may further be configured to receive a fifth set of data associated with the required linear force and required displacement of the head of the humerus bone of the patient.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent that the present teachings may be practiced without such details. In other instances, well-known methods, procedures, components, and/or circuitry have been described at a relatively high-level, without detail, in order to avoid unnecessarily obscuring aspects of the present teachings. The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown but is to be accorded the widest possible scope consistent with the principles and features disclosed herein.

Herein is disclosed an exemplary rehabilitation system for robotized mobilization of a human glenohumeral joint of a patient. The exemplary system provides a facility that may enable a physician and/or a physiotherapist to implement linear movement of a head of a humerus bone along a glenohumeral joint in a controlled procedure as a remedy for glenohumeral joint hypomobility. The exemplary rehabilitation system may have a limb gripping member that receives an arm of a patient and secure that in a predetermined position. Furthermore, the exemplary rehabilitation system may further have an actuating mechanism that may be responsible to urge a head of a humerus bone of a patient to move along an axis parallel with a midline of the patient's body.

Figure 1:
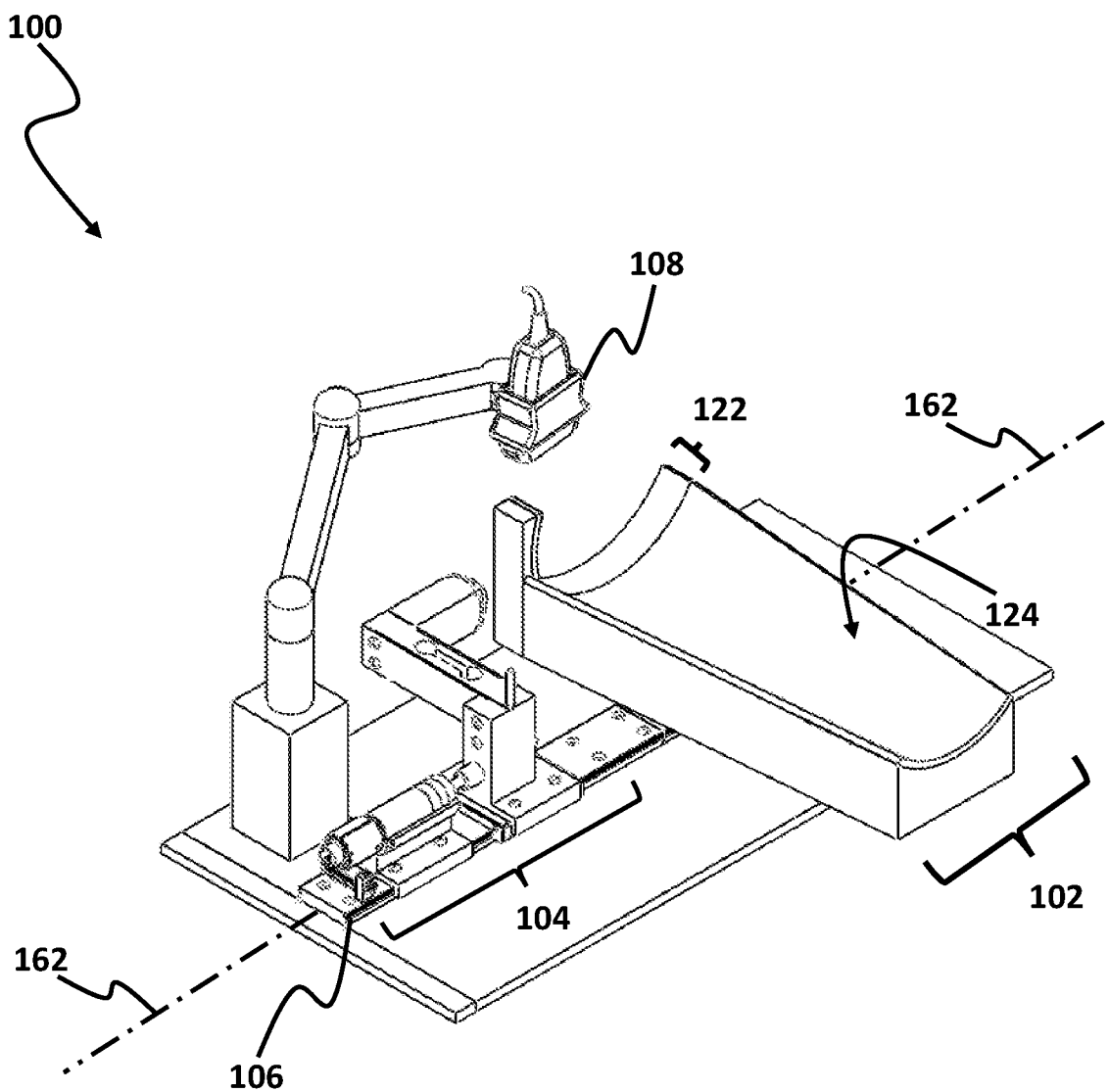
FIG. 1 illustrates an exemplary rehabilitation system, consistent with one or more exemplary embodiments of the present disclosure.
Figure 2:
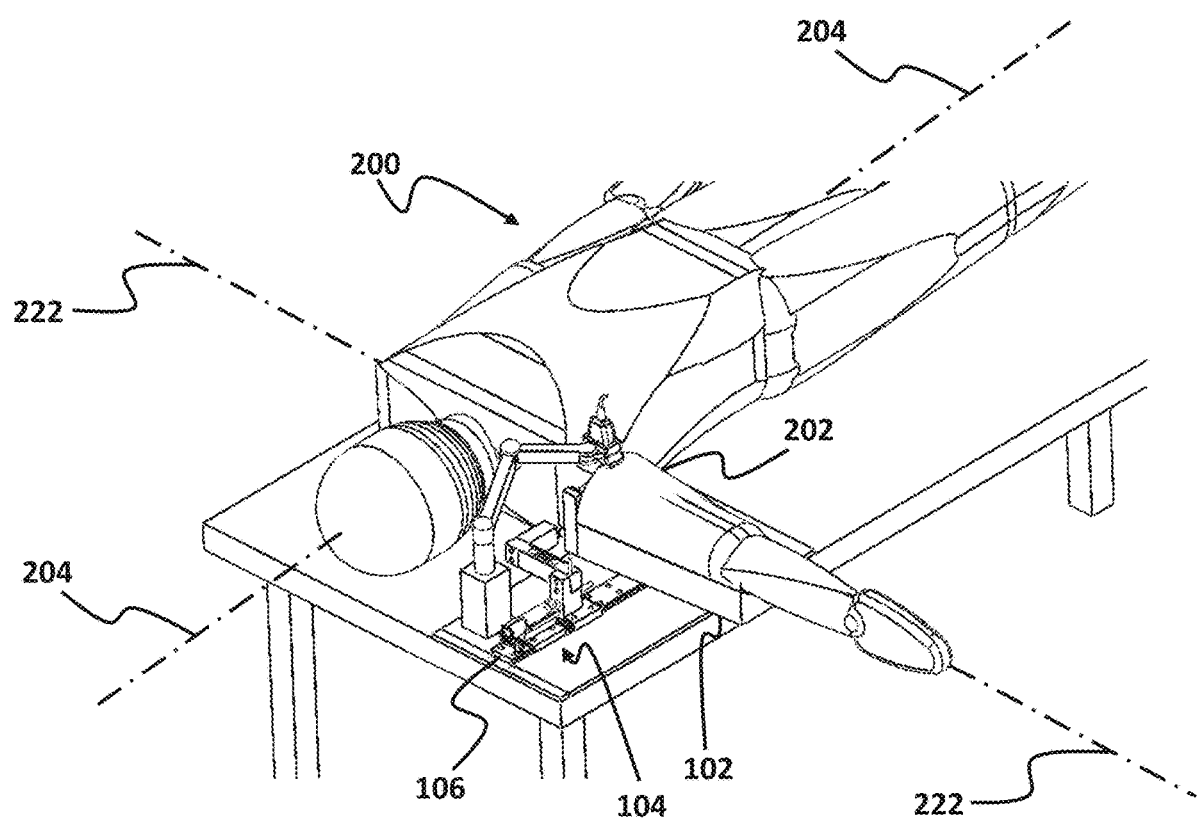
FIG. 2 illustrates an exemplary rehabilitation system when an arm of a patient is inserted into a limb gripping member of the rehabilitation system, consistent with one or more exemplary embodiments of the present disclosure.

FIG. 1 shows an exemplary rehabilitation system 100, consistent with one or more exemplary embodiments of the present disclosure. In an exemplary embodiment, rehabilitation system 100 may include a limb gripping member 102. In an exemplary embodiment, limb gripping member 102 may be able to receive an arm of a patient and may also secure the arm of the patient in a predetermined position. FIG. 2 shows rehabilitation system 100 when an arm 202 of a patient 200 is inserted into limb gripping member 102, consistent with one or more exemplary embodiments of the present disclosure. As shown in FIG. 2, it may be understood that patient 200 may lie in a supine position and insert his/her hand into limb gripping member 102. In an exemplary embodiment, supine position may refer to a position at which patient 200 may be lying horizontally with their face and torso facing up (as shown in FIG. 2).

In an exemplary embodiment, limb gripping member 102 may include a crescent-shaped section 122 configured to grasp arm 202 of patient 200. In an exemplary embodiment, limb gripping member 102 may also include a groove-shaped section 124 configured to secure arm 202 and elbow of patient 200.

As shown in FIG. 2, limb gripping member 102 may secure arm 202 of patient 200 in a perpendicular abducted position. In an exemplary embodiment, abduction may refer to movement of arm 202 away from the midline of patient's 200 body. Furthermore, in an exemplary embodiment, predetermined position may be a position at which a main longitudinal axis 222 of arm 202 is substantially perpendicular to a main axis 204 of patient's 200 body. In an exemplary embodiment, main axis 204 of patient's 200 body may be the same as a midline of patient's 200 body.

Figure 3:
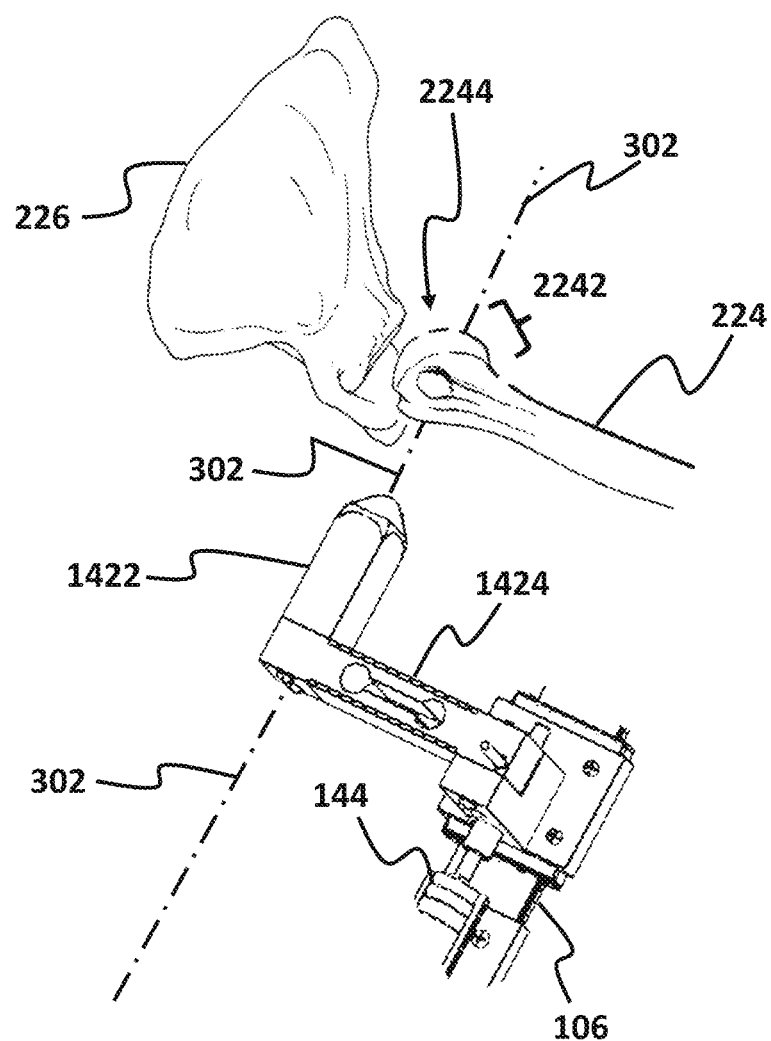
FIG. 3 illustrates an exemplary rehabilitation system with a humerus bone of a patient, consistent with one or more exemplary embodiments of the present disclosure.

FIG. 3 shows an exemplary rehabilitation system with a humerus bone of a patient, consistent with one or more exemplary embodiments of the present disclosure. As shown in FIGS. 1-3, in an exemplary embodiment, rehabilitation system 100 may further include an actuating mechanism 104. In an exemplary embodiment, actuating mechanism 104 may urge a head 2242 of a humerus bone 224 of patient 200 to glide along a first axis 302 by applying a linear force to a proximal end 2244 of humerus bone 224 of patient 220. In an exemplary embodiment, first axis 302 may be substantially parallel to main axis 204 of patient's 200 body.

As shown in FIG. 1 and FIG. 2, rehabilitation system 100 may further include a guide rail 106. In an exemplary embodiment, limb gripping member 102 may be mounted slidably onto guide rail 106. In an exemplary embodiment, it may be understood that a component or device that is disposed and/or mounted slidably is capable of translational movement. In an exemplary embodiment, guide rail 106 may limit movements of patient's arm 202 and limb gripping member 102 to a linear movement along a second axis 162. In an exemplary embodiment, second axis 162 may be the same as a main longitudinal axis of guide rail 106. In an exemplary embodiment, second axis 162 may be substantially parallel to first axis 302.

Figure 4:
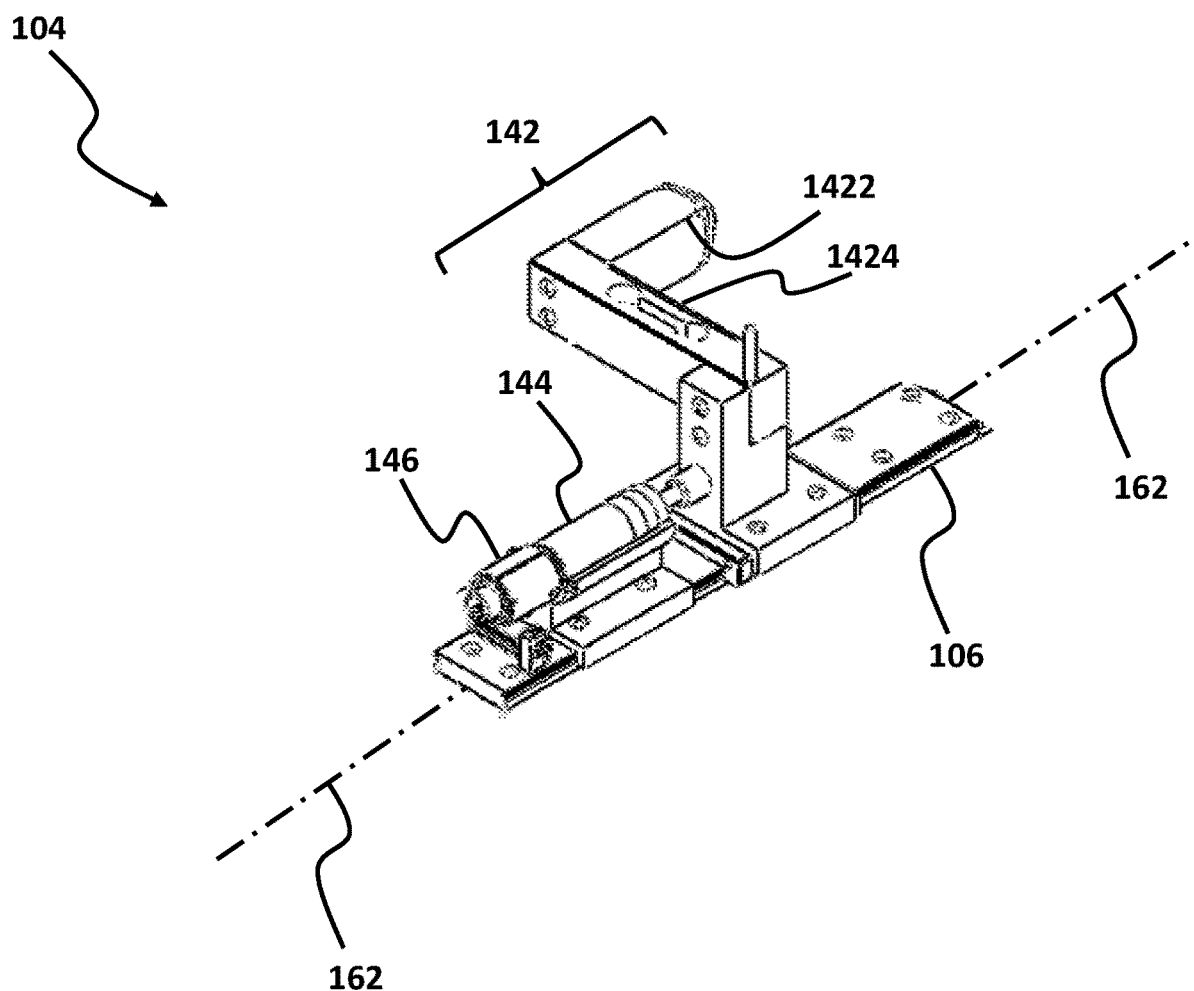
FIG. 4 illustrates an exemplary actuating mechanism of a rehabilitation system, consistent with one or more exemplary embodiments of the present disclosure.

FIG. 4 shows an exemplary actuating mechanism of a rehabilitation system, consistent with one or more exemplary embodiments of the present disclosure. As shown in FIG. 4, actuating mechanism 104 may include a force applying assembly 142. In an exemplary embodiment, force applying assembly 142 may be mounted slidably onto guide rail 106. In an exemplary embodiment, guide rail 106 may limit movements of force applying assembly 142 to a linear movement along second axis 162. In an exemplary embodiment, force applying assembly 142 may include a stylus 1422. In an exemplary embodiment, stylus 1422 may push head 2242 of humerus bone 224 of patient 200 to move along first axis 302 responsive to actuator 144 moving force applying assembly 142 on guide rail 106 and along second axis 162.

In an exemplary embodiment, stylus 1422 may further be aligned with head 2242 of humerus bone 224 of patient 200 responsive to arm 202 of patient 200 being inserted into limb gripping member 102. In an exemplary embodiment, stylus 1422 may be positioned relative to limb gripping member 102 in a way such that when arm 202 of patient 200 is inserted into limb gripping member 102, head 2242 of humerus bone 224 of patient 200 is placed in front of stylus 1422 and consequently is aligned with stylus 1422. In an exemplary embodiment, force applying assembly 142 may further include a position adjuster mechanism that allow the physician/physiotherapist to align stylus 1422 with head 2242 of humerus bone 224 of patient 200 after that arm 202 of patient 200 is inserted into limb gripping member 102.

As shown in FIG. 4, in an exemplary embodiment, force applying assembly 142 may further include a force measuring member 1424. In an exemplary embodiment, force measuring member 1424 may be disposed between actuator 144 and stylus 1422. In an exemplary embodiment, force measuring member 1424 may measure a linear force applied to proximal end 2244 of humerus bone 224 of patient 200 from stylus 1422. In an exemplary embodiment, force measuring member 1424 may further transmit a first set of data to one or more processors (not shown) associated with the measured linear force applied to proximal end 2244 of humerus bone 224 of patient 200 from stylus 1422. In an exemplary embodiment, force measuring member 1424 may include a dynamometer or alternatively include a load cell. In an exemplary embodiment, force measuring member 1424 may measure a force interacted between actuator 144 and stylus 1422. In an exemplary embodiment, it may be understood that the force interacted between actuator 144 and stylus 1422 may be easily converted to a force that may be applied to head 2242 of humerus bone 224 of patient 200 from stylus 1422

In an exemplary embodiment, actuating mechanism 104 may further include an actuator 144 fixedly attached to guide rail 106. In an exemplary embodiment, actuator 144 may apply a linear force along first axis 302 to proximal end 2244 of humerus bone 224 of patient 200. In an exemplary embodiment, actuator 144 may apply a linear force along first axis 302 to proximal end 2244 of humerus bone 224 of patient 200 through moving force applying assembly 142 on guide rail 106 and along second axis 162.

As shown in FIG. 4, in an exemplary embodiment, actuating mechanism 104 may further include an encoder 146. In an exemplary embodiment, encoder 146 may be coupled to actuator 144. In an exemplary embodiment, encoder 146 may measure an amount of linear movement of force applying assembly 142 along second axis 162. Furthermore, in an exemplary embodiment, encoder 146 may further transmit a second set of data to one or more processors associated with the linear movement of force applying assembly 142 along second axis 162. In an exemplary embodiment, it may be understood that an amount of the linear movement of force applying assembly 142 along second axis 162 that may be measured utilizing encoder 146 may be the same as head 2242 of humerus bone 224 of patient 200 displacement along first axis 302.

Referring back to FIG. 1, in an exemplary embodiment, rehabilitation system 100 may further include an ultrasound imaging system 108. In an exemplary embodiment, ultrasound imaging system 108 may capture a third set of data associated with position of head 2242 of humerus bone 224 along first axis 302. Furthermore, ultrasound imaging system 108 may transmit the third set of data to one or more processors. In an exemplary embodiment, the third set of data may be a plurality of ultrasound images. In an exemplary embodiment, it may be understood that the plurality of ultrasound images may represent a valid and objective measurement of head 2242 of humerus bone 224 of patient 200 displacement relative to a glenoid fossa of scapula bone 226.

In an exemplary embodiment, one or more processors (not shown) may receive the first set of data, receive the second set of data, and receive the third set of data. Furthermore, the one or more processors may transmit a fourth set of data to actuator 144 based on the received first set of data, received second set of data, and received third set of data. For purpose of reference, it may be understood that for each specific patient and specific period of treatment duration, a respective force and a respective head of the humerus bone displacement may be prescribed from a physician and/or physiotherapist. In an exemplary embodiment, the one or more processors may receive a data from a physician and/or physiotherapist that is associated with a required force and a required head of a humerus bone displacement. The one or more processors may then transmit commands to actuator 144 based on the received data from force measuring member 1424, encoder 146, and physician and/or physiotherapist.

Figure 5:
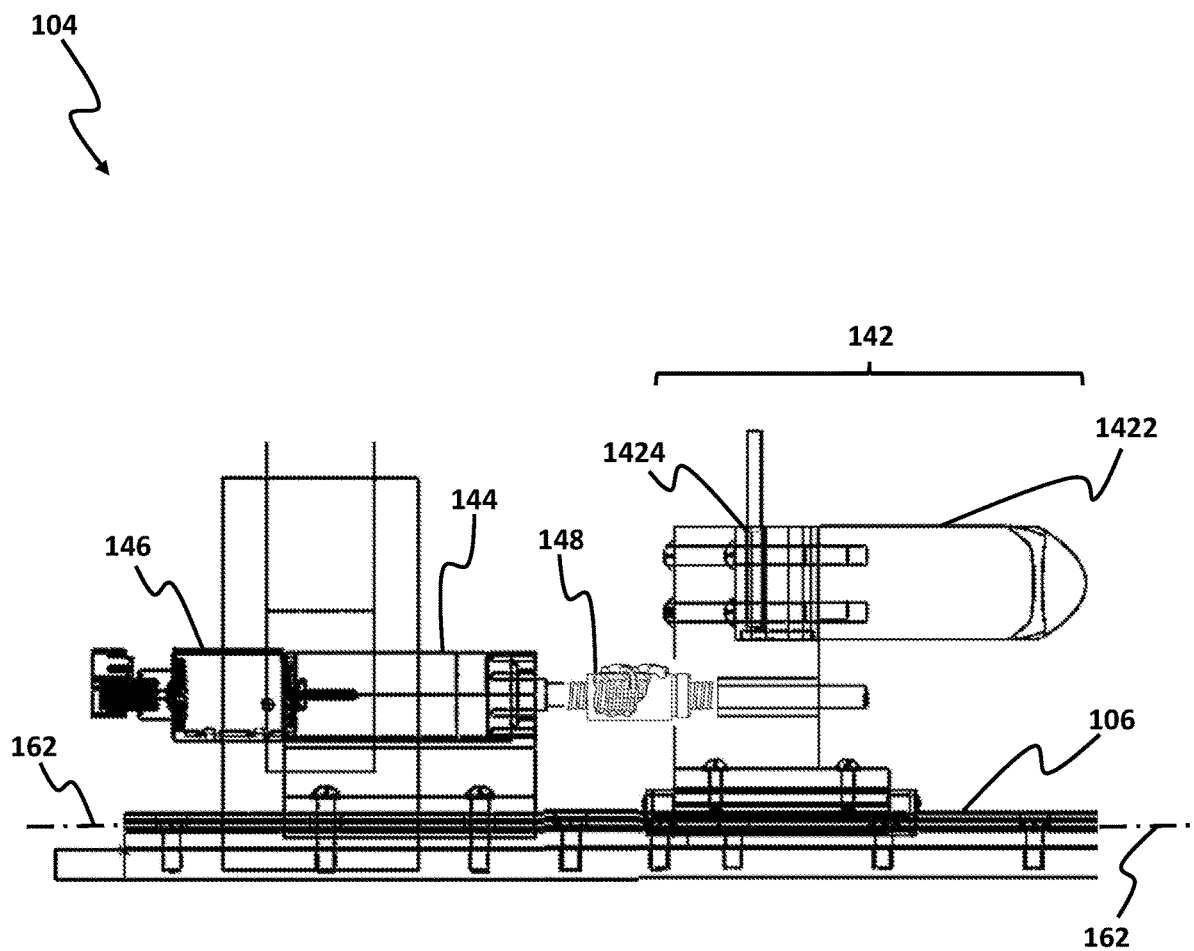
FIG. 5 illustrates a side view of an exemplary actuating mechanism of a rehabilitation system, consistent with one or more exemplary embodiments of the present disclosure.

FIG. 5 shows a side view of an exemplary actuating mechanism of a rehabilitation system, consistent with one or more exemplary embodiments of the present disclosure. As shown in FIG. 5, in an exemplary embodiment, force applying assembly 142 may be coupled to actuator 144 utilizing a ball screw mechanism 148. In an exemplary embodiment, ball screw mechanism 148 may convert a rotational movement of actuator 144 to a linear movement of force applying assembly 142 along second axis 162.

Figure 6:
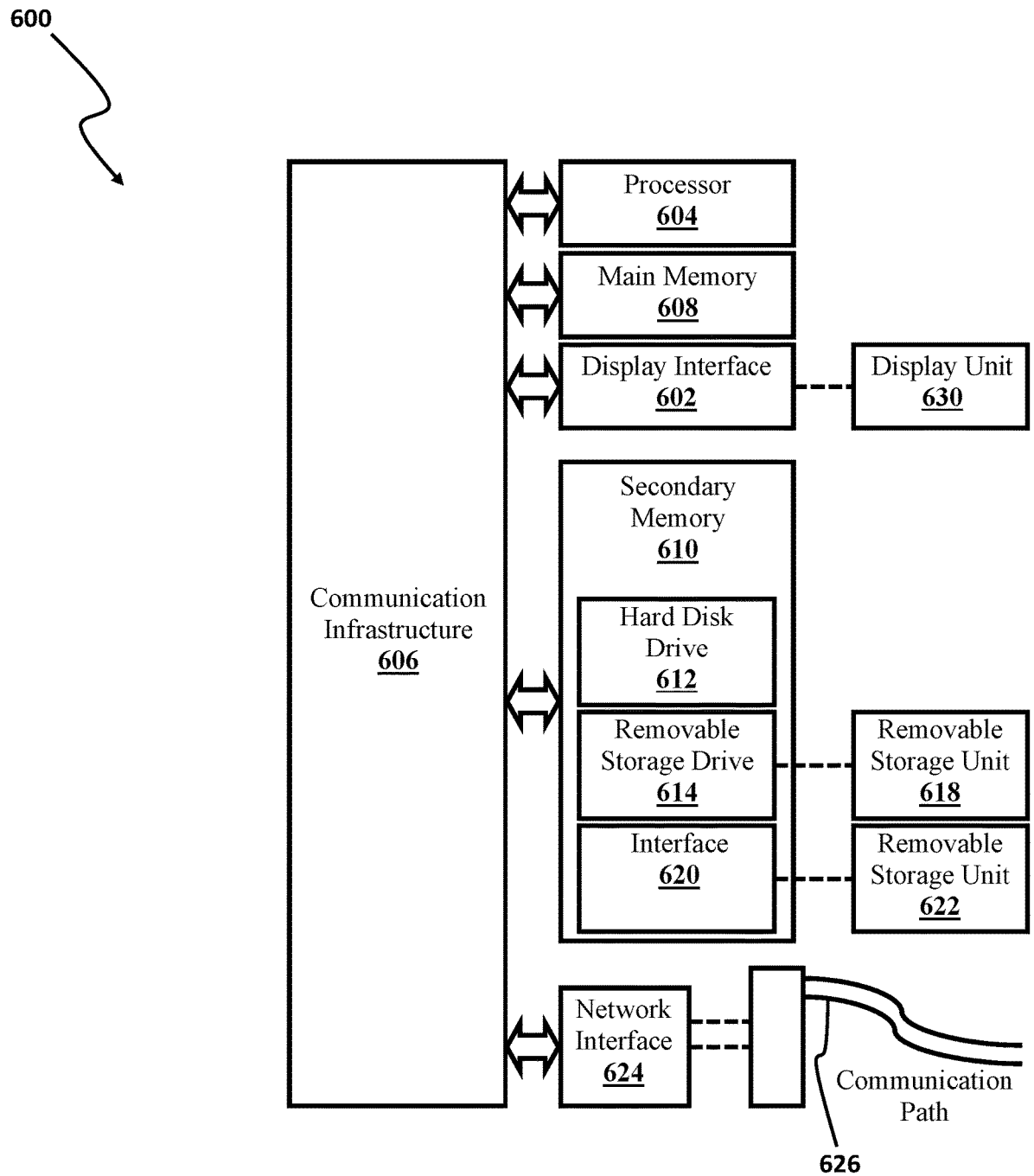
FIG. 6 illustrates an exemplary embodiment of a processing unit, consistent with one or more exemplary embodiments of the present disclosure.

FIG. 6 shows an exemplary embodiment of processing unit 600 in which an exemplary embodiment of the present disclosure, or portions thereof, may be implemented as computer-readable code, consistent with one or more exemplary embodiments of the present disclosure. For example, an exemplary tele-robotic surgical system may be implemented in processing unit 600 using hardware, software, firmware, tangible computer readable media having instructions stored thereon, or a combination thereof and may be implemented in one or more computer systems or other processing systems. In an exemplary embodiment, the one or more processors as discussed with respect to FIGS. 4-5 may be similar to processing unit 600 of FIG. 6.

If programmable logic is used, such logic may execute on a commercially available processing platform or a special purpose device. One of ordinary skill in the art may appreciate that an exemplary embodiment of the disclosed subject matter can be practiced with various computer system configurations, including multi-core multiprocessor systems, minicomputers, mainframe computers, computers linked or clustered with distributed functions, as well as microcontrollers, pervasive or miniature computers that may be embedded into virtually any device.

For instance, a computing device having at least one processor device and a memory may be used to implement the above-described embodiments. A processor device may be a single processor, a plurality of processors, or combinations thereof. Processor devices may have one or more processor "cores."

An exemplary embodiment of the present disclosure is described in terms of this example processing unit 600. After reading this description, it will become apparent to a person skilled in the relevant art how to implement the present disclosure using other computer systems and/or computer architectures. Although operations may be described as a sequential process, some of the operations may in fact be performed in parallel, concurrently, and/or in a distributed environment, and with program code stored locally or remotely for access by single or multi-processor machines. In addition, in some embodiments the order of operations may be rearranged without departing from the spirit of the disclosed subject matter.

Processor device 604 may be a special purpose or a general-purpose processor device. As will be appreciated by persons skilled in the relevant art, processor device 604 may also be a single processor in a multi-core/multiprocessor system, such system operating alone, or in a cluster of computing devices operating in a cluster or server farm. In an exemplary embodiment, processor device 604 may be connected to a communication infrastructure 606, for example, a bus, message queue, network, or multi-core message-passing scheme.

In an exemplary embodiment, processing unit 600 may also include a main memory 608, for example, random access memory (RAM), and may also include a secondary memory 610. In an exemplary embodiment, processing unit 600 may also include a display interface 602 and a display unit 630. In an exemplary embodiment, secondary memory 610 may include a hard disk drive 612, and a removable storage drive 614. In an exemplary embodiment, removable storage drive 614 may include a floppy disk drive, a magnetic tape drive, an optical disk drive, a flash memory, or the like. In addition, removable storage drive 614 may read from and/or write to a removable storage unit 618 in a well-known manner. In an exemplary embodiment, removable storage unit 618 may include a floppy disk, magnetic tape, optical disk, etc., which may be read by and written to by removable storage drive 614. As will be appreciated by persons skilled in the relevant art, removable storage unit 618 may include a computer usable storage medium having stored therein computer software and/or data.

In alternative implementations, secondary memory 610 may include other similar means for allowing computer programs or other instructions to be loaded into processing unit 150. Such means may include, for example, a removable storage unit 622 and an interface 620. Examples of such means may include a program cartridge and cartridge interface (such as that found in video game devices), a removable memory chip (such as an EPROM, or PROM) and associated socket, and other removable storage units 622 and interfaces 620 which allow software and data to be transferred from removable storage unit 622 to processing unit 600.

In an exemplary embodiment, processing unit 600 may also include a communications interface 624. Communications interface 624 may allow software and data to be transferred between processing unit 600 and external devices. In an exemplary embodiment, communications interface 624 may include a modem, a network interface (such as an Ethernet card), a communications port, a PCMCIA slot and card, or the like. Software and data transferred via communications interface 624 may be in the form of signals, which may be electronic, electromagnetic, optical, or other signals capable of being received by communications interface 624. These signals may be provided to communications interface 624 via a communications path 626. In an exemplary embodiment, communications path 626 may carry signals and may be implemented using wire or cable, fiber optics, a phone line, a cellular phone link, an RF link or other communications channels.

In this document, the terms "computer program medium" and "computer usable medium" are used to generally refer to media such as removable storage unit 618, removable storage unit 622, and a hard disk installed in hard disk drive 612. Computer program medium and computer usable medium may also refer to memories, such as main memory 608 and secondary memory 610, which may be memory semiconductors (e.g. DRAMs, etc.).

In some exemplary embodiment, computer programs (also called computer control logic) may be stored in main memory 608 and/or secondary memory 610. Computer programs may also be received via communications interface 624. Such computer programs, when executed, enable processing unit 600 to implement the present disclosure as discussed herein. In particular, the computer programs, when executed, may enable processor device 604 to implement the processes of the present disclosure. Accordingly, such computer programs represent controllers of processing unit 600. Where the present disclosure is implemented using software, the software may be stored in a computer program product and loaded into processing unit 600 using removable storage drive 614, interface 620, and hard disk drive 612, or communications interface 624.

Embodiments of the present disclosure may also be directed to computer program products including software stored on any computer useable medium. Such software, when executed in one or more data processing devices, causes a data processing device(s) to operate as described herein. An exemplary embodiment of the present disclosure may employ any computer useable or readable medium. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, and optical storage devices, MEMS, nano-technological storage device, etc.).

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study, except where specific meanings have otherwise been set forth herein. Relational terms such as "first" and "second" and the like may be used solely to distinguish one entity or action from another without necessarily requiring or implying any actual such relationship or order between such entities or actions. The terms "comprises," "comprising," or any other variation thereof, as used herein and in the appended claims are intended to cover a non-exclusive inclusion, encompassing a process, method, article, or apparatus that comprises a list of elements that does not include only those elements but may include other elements not expressly listed to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is not intended to be used to interpret or limit the scope or meaning of the claims. In addition, in the foregoing Detailed Description, it can be seen that various features are grouped together in various implementations. Such grouping is for purposes of streamlining this disclosure and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into this Detailed Description, with each claim standing on its own as a separately claimed subject matter.

While various implementations have been described, the description is intended to be exemplary, rather than limiting and it will be apparent to those of ordinary skill in the art that many more implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in the light of the attached claims and their equivalents. Also, various modifications and changes may be made within the scope of the attached claims.

What is claimed is:

1. A rehabilitation system for robotized mobilization of a human glenohumeral joint of a patient, the rehabilitation system comprising:
   a limb gripping member configured to:
      receive an arm of a patient; and
      secure the arm of the patient in a predetermined position;
   an actuating mechanism configured to urge a head of a humerus bone of the patient to move along a first axis by applying a linear force to a proximal end of the humerus bone of the patient, the head of the humerus bone of the patient located at the proximal end of the humerus bone of the patient; and
   a guide rail, the limb gripping member mounted slidably onto the guide rail, the guide rail configured to limit movements of the patient's arm and the limb gripping member to a linear movement along a second axis,
   wherein the actuating mechanism comprises:
      a force applying assembly mounted slidably onto the guide rail, the guide rail configured to limit movements of the force applying assembly to a linear movement along the second axis; and
      an actuator fixedly attached to the guide rail, the actuator configured to apply a linear force along the first axis to the proximal end of the humerus bone of the patient by moving the force applying assembly on the guide rail and along the second axis.

2. The rehabilitation system of claim 1, wherein the first axis is parallel with the second axis.

3. The rehabilitation system of claim 1, wherein the force applying assembly comprises:
   a stylus configured to push the head of the humerus bone of the patient to move along the first axis responsive to the actuator moving the force applying assembly on the guide rail and along the second axis, the stylus further configured to be aligned with the head of the humerus bone of the patient responsive to the arm of the patient inserted into the limb gripping member; and
   a force measuring member disposed between the actuator and the stylus, the force measuring member configured to:
      measure the linear force applied to the proximal end of the humerus bone of the patient from the stylus; and transmit a first set of data to one or more processors associated with the measured linear force applied to the proximal end of the humerus bone of the patient from the stylus.

4. The rehabilitation system of claim 3, wherein the actuating mechanism further comprises an encoder coupled to the actuator, the encoder configured to:
   measure an amount of the linear movement of the force applying member along the second axis; and
   transmit a second set of data to the one or more processors associated with the amount of the linear movement of the force applying assembly along the second axis.

5. The rehabilitation system of claim 4 further comprises an ultrasound imaging system configured to:
   capture a third set of data associated with a position of the head of the humerus bone along the first axis; and
   transmit the third set of data to the one or more processors.

6. The rehabilitation system of claim 5, wherein the one or more processors are configured to:
   receive the first set of data;
   receive the second set of data;
   receive the third set of data; and
   transmit a fourth set of data to the actuator based on the received first set of data, the received second set of data, and the received third set of data.

7. The rehabilitation system of claim 6, wherein the force applying assembly is coupled to the actuator utilizing a ball screw mechanism, the ball screw mechanism configured to convert a rotational movement of the actuator to a linear movement of the force applying assembly along the second axis.

8. The rehabilitation system of claim 7, wherein the force measuring member comprises one of a load cell and a dynamometer.

9. The rehabilitation system of claim 8, wherein the one or more processors are further configured to receive a fifth set of data from a physician, the fifth set of data associated with a required linear force and a required displacement of the head of the humerus bone of the patient.

10. The rehabilitation system of claim 9, wherein the limb gripping member further comprises:
    a crescent-shaped section configured to grasp the arm of the patient; and
    a groove-shaped section configured to secure the arm and an elbow of the patient.

11. The rehabilitation system of claim 10, wherein the third set of data comprises at least one ultrasound image of the head of the humerus bone of the patient.

* * * * *